United States Patent
Pianca et al.

(10) Patent No.: US 7,004,948 B1
(45) Date of Patent: Feb. 28, 2006

(54) CRANIAL SEALING PLUG

(75) Inventors: Anne M. Pianca, Valencia, CA (US); Carla M. Mann, Los Angeles, CA (US); Tom Xiaohai He, Simi Valley, CA (US); Michael Dogali, Newport Beach, CA (US)

(73) Assignee: Advanced Bionics Corporation, Valencia, CA (US)

( * ) Notice: Subject to any disclaimer, the term of this patent is extended or adjusted under 35 U.S.C. 154(b) by 566 days.

(21) Appl. No.: 10/052,331

(22) Filed: Jan. 18, 2002

Related U.S. Application Data (60) Provisional application No. 60/265,770, filed on Jan. 31, 2001.

(51) Int. Cl.
 *A61B 19/00* (2006.01)
 *A61B 5/04* (2006.01)
 *A61N 1/00* (2006.01)

(52) U.S. Cl. .................. 606/129; 607/116; 600/378
(58) Field of Classification Search .................. 606/72, 606/129; 607/116; 600/378
 See application file for complete search history.

(56) References Cited

U.S. PATENT DOCUMENTS

| | | |
|---|---|---|
| 3,918,461 A | 11/1975 | Cooper |
| 4,245,645 A | 1/1981 | Arseneault et al. |
| 4,328,813 A | 5/1982 | Ray |
| 4,350,159 A | 9/1982 | Gouda |
| 4,826,487 A | 5/1989 | Winter |
| 4,850,359 A | 7/1989 | Putz |
| 4,931,056 A | 6/1990 | Ghajar et al. |
| 4,955,891 A | 9/1990 | Carol |
| 4,998,938 A | 3/1991 | Ghajar et al. |
| 5,201,737 A | 4/1993 | Leibinger et al. |
| 5,300,080 A | 4/1994 | Clayman et al. |
| 5,330,485 A | 7/1994 | Clayman et al. |
| 5,464,446 A | 11/1995 | Dreessen et al. |
| 5,503,164 A * | 4/1996 | Friedman ................ 128/898 |
| 5,549,620 A * | 8/1996 | Bremer .................. 606/151 |
| 5,707,373 A | 1/1998 | Sevrain et al. |
| 5,843,150 A | 12/1998 | Dreessen et al. |
| 5,865,842 A | 2/1999 | Knuth et al. |
| 5,927,277 A | 7/1999 | Baudino et al. |
| 5,954,687 A | 9/1999 | Baudino |
| 6,006,124 A | 12/1999 | Fischell et al. |
| 6,044,304 A | 3/2000 | Baudino |
| 6,050,998 A | 4/2000 | Fletcher |

(Continued)

*Primary Examiner*—Gary Jackson
(74) *Attorney, Agent, or Firm*—Victoria A. Poissant; Bryant R. Gold (57) ABSTRACT

Various embodiments of a burr hole plug assembly offer significant improvements for allowing lead and/or cannula access through a burr hole drilled through a patient's skull in connection with a Deep Brain Stimulation system, and subsequent sealing of such burr hole. The various burr hole plug assemblies described: (a) accommodate various burr hole sizes and provide a secure fit in the burr hole; (b) accommodate various locations for lead positioning and adjustment; (c) allow the lead to remain in a static position when the burr hole plug assembly is placed; (d) protect the lead from fracture at the exit location of the plug; (e) remain flush with the skull to avoid skin erosion and to eliminate unsightly flange protrusion from the patients' skull; (f) adequately hold the lead in place over time; and (g) provide a selection of various types of burr hole plug assemblies and sizes for use by the implanting surgeon, thereby eliminating the need for surgeons to resort to custom plugs and plug assemblies made in the operating room specifically to fit a given patient.

9 Claims, 9 Drawing Sheets

U.S. PATENT DOCUMENTS 6,126,663 A * 10/2000 Hair .......................... 606/72
6,321,104 B1 11/2001 Gielen et al.
6,482,182 B1 11/2002 Carroll et al.
6,572,623 B1 * 6/2003 Birchall et al. ............... 606/76

* cited by examiner

CRANIAL SEALING PLUG

The present application claims the benefit of U.S. Provisional Application Ser. No. 60/265,770, filed Jan. 31, 2001, which application is incorporated herein by reference.

BACKGROUND OF THE INVENTION

The present invention relates to the field of implantable medical devices, including implantable electrodes. More particularly, the invention relates to cranial sealing plugs used to seal a hole made through the skull of a patient for the purpose of inserting a medical device and/or electrode into the brain. Even more particularly, the invention relates to burr hole plugs which are flush with the surface of the skull. The embodiments described in the present invention may be used with a wide variety of burr hole sizes, which burr holes are typically used to provide electrode or lead access to the brain in connection with a Deep Brain Stimulation (DBS) system. It is to be noted, however, that the burr hole plug embodiments of the invention may also be used to seal holes made for the passage of other objects into the brain, such as ablation catheters, drug delivery catheters, tissue delivery catheters, and the like.

Deep Brain Stimulation is a medical procedure which involves access to the brain through a burr hole placed in the skull for treating Parkinson's Disease, Essential Tremor, dystonia, chronic pain relief, and potentially the treatment of choice for other disorders. A typical surgical approach may include the following steps, of which only steps 8, 31, and 32 relate directly to the present invention:

1. Attach the stereotactic frame on patient's head.
2. Obtaining an image of the various brain structures with MRI or equivalent imaging modality of patient with stereotactic frame.
3. Obtaining target identification using a planning software.
4. Positioning the patient with stereotactic frame in head rest.
5. Cutting the skin flap, exposing the working surface area of cranium using scalp clips.
6. Placing the stereotactic arc with target coordinate settings and identifying the location on the skull for creation of the burr hole.
7. Removing the arc and drilling a burr hole.
8. Placing the base of the burr hole plug.
9. Placing the stereotactic arc with microelectrode recording drive attached and appropriate stereotactic frame adaptor inserted into instrument guide.
10. Inserting the recording microelectrode cannula and insertion rod approximately 25 mm above the target.
11. Removing the recording microelectrode insertion rod, while leaving recording microelectrode cannula in place.
12. Inserting the recording microelectrode such that the tip is flush with the tip of the recording microelectrode cannula.
13. Attaching the connector pin of the recording microelectrode to the microelectrode recording system.
14. Starting approximately 25 mm above target, begin the microelectrode recording tract using the microdrive to advance the microelectrode at a specified rate.
15. If the target is identified, prepare to place the stimulating macroelectrode and proceed with step 16, if the target is not identified proceed with the following:
    a. Using recording results and pre-operative imaging, determining a new set of coordinates for the theoretical target.
    b. Disconnecting recording microelectrode from the microelectrode recording system.
    c. Removing the recording microelectrode cannula and recording microelectrode.
    d. Continuing with the surgical process at step 10 above.
16. Removing the recording microelectrode cannula and recording microelectrode.
17. Inserting a larger diameter insertion cannula and rod (the tip of the slit insertion cannula and rod will be at a location 25 mm above target).
18. Removing the insertion rod, while leaving insertion cannula in place.
19. Inserting a stimulating macroelectrode, and advancing to the target stimulation site identified in step 15 above.
20. Using macrostimulation, simulating the stimulation of the chronic DBS lead to ensure proper results.
21. Removing the stimulating macroelectrode and cannula.
22. Inserting an insertion cannula and rod that accommodates the DBS lead.
23. Removing the insertion rod.
24. Inserting the lead with stylet through the insertion cannula.
25. Advancing the lead with the stylet to the target stimulation site.
26. Once it is determined that the lead has been advanced to the desired target location, connecting the connector of the lead to a trial stimulator.
27. Performing the desired stimulation and measurements using any one or combination of the four electrodes.
28. If results are favorable, then begin removal of the insertion cannula and the stylet, and proceed with step 29, if the results are not favorable then proceed with the following:
    a. Using the macrostimulation results, microelectrode recording results, and pre-operative imaging, determine a new set of coordinates for the theoretical target.
    b. Removing the lead and stylet.
    c. Removing the insertion cannula.
    d. Adjusting the coordinates of the stereotactic frame.
    e. Continuing with the surgical process at step 10 above.
29. Removing the stylet followed by the insertion cannula.
30. Using macrostimulation verifying that microdislodgement of the lead has not occurred.
31. Locking the lead in the burr hole plug.
32. Placing the burr hole plug cap.

Several inventions are known in the art that relate to burr hole plugs used for DBS application. As used herein, the term "burr hole plugs" relates to any device or assembly or system that includes one or more components for insertion into a burr hole. Typically, a burr hole plug assembly includes at least two components: a ring or grommet-like element that is inserted into the hole first so as to protect the edges of the burr hole (item 8 above), and a cap or plug device that is inserted into the ring or grommet-like element after the lead has been positioned in order to secure the lead and plug the hole.

By way of example, in U.S. Pat. No. 6,044,304, entitled Burr Ring with Integral Lead/Catheter Fixation Device, a burr ring that is secured to the skull portion of the brain is described. Patent '304 is incorporated herein by reference. The burr hole plug described has an aperture capable of accepting a lead through a septum. In addition the burr hole plug has an upper flange portion and circumferential ribs used to position the plug in the cranium. The flange feature prevents the burr hole plug from being flush with the surface of the skull. Use of the ribs in the manner suggested indicates that the material from which the plug and ribs are made is relatively rigid.

Another burr hole plug known in the art is described in U.S. Pat. No. 6,006,124, which patent is incorporated herein by reference. The '124 patent describes electrically connecting an implantable control module to a brain electrode. The '124 patent also describes a method of placing brain electrodes beneath the scalp. No mention is made in the '124 patent of a mechanical connection for the lead, nor of the mechanical stability of the burr hole plug.

Still, with reference to U.S. Pat. No. 5,954,687, which patent is incorporated herein by reference, an apparatus is disclosed for securing a catheter within a burr hole. The apparatus described in the '687 patent has a series of spaced septum elements that can be selectively penetrated for fluid communication with a reservoir in the apparatus. The main objective of the apparatus is to allow fluid access to the patients' brain through a burr hole. Anchoring of the device is not taught, and there are a limited predetermined number of septum holes that can be accessed, thereby limiting use of the apparatus.

In yet another example, U.S. Pat. No. 5,927,277, which patent is also incorporated herein by reference, describes a burr hole ring for retaining a probe relative to the skull. The burr hole ring has an engaging member with holes to receive a probe. The '277 patent also describes a method for securing a device at a desired orientation within the burr hole. Since a fixed spacing between holes is described, this limits the number of locations that the device can be placed through the burr hole. The device described in the '277 patent consists of several parts one of which contains a flange.

U.S. Pat. No. 5,865,842, incorporated herein by reference, teaches a system and method for anchoring a lead in a burr hole. Such system consists of a base-plate, adaptor, seal, and screw cap. The lead is anchored mechanically at the burr hole at a 90 degree angle relative to the burr hole. A flange protrudes from the burr hole of the skull.

In U.S. Pat. No. 5,843,150, incorporated herein by reference, an annular clamping means with a compressible feedthrough member for receiving a lead is described. The described order for anchoring the lead includes making the burr hole, inserting the plug ring, inserting the lead, and engaging the clamping member. The embodiments described show an annular clamping means with protruding flanges.

Other burr hole plug assemblies, and features of burr hole plugs are taught, e.g., in U.S. Pat. No. 5,464,446 (burr hole plug with a central lumen and a cap that engages with the flange of the plug); U.S. Pat. No. 4,998,938 (a device that facilitates insertion of an instrument into a patient's cranial cavity); U.S. Pat. No. 4,328,813 (a burr hole plug with a cap that anchors the lead); and U.S. Pat. No. 4,245,645 (a probe and system that is used to perform stereoelectroencephalographic exploration). The burr hole plug applications described in these additional patents, including many lead insertion techniques, may also be used with the present invention. For that reason, the '466, 938, '813 and '645 patents are incorporated herein by reference.

Despite the various types of burr hole plugs known in the art, as illustrated by the examples cited above, significant improvements are still possible and desirable, particularly relative to a burr hole plug assembly that: (a) can accommodate various burr hole sizes and a secure fit in the burr hole; (b) can accommodate various locations for lead positioning and adjustment; (c) can allow the lead to remain in a static position when the burr hole plug is placed; (d) protect the lead from fracture at the exit location of the plug; (e) is flush with the skull to avoid skin erosion and to eliminate any unsightly flange protrusion from the patients' skull (which can be especially important in the population of older balding males); (f) adequately holds the lead in place over time, eliminating the need for additional surgeries; and (g) provides a selection of various types of burr hole plugs that may be used by the medical industry, thereby eliminating the need for physicians to resort to custom devices.

It is thus seen that there is a continual need for a variety of burr hole plug assemblies and lead securing methods for use therewith.

SUMMARY OF THE INVENTION

The present invention addresses the above and other needs by providing a reliable method of sealing a burr hole using a sealing cranial plug that can accommodate various burr hole sizes and lead securing methods.

The invention disclosed and claimed herein provides various embodiments of cranial sealing burr hole plug assemblies. Such assemblies accommodate various burr hole sizes, provide various lead positioning features, are adjustable and compressible, provide a design that is flush with the skull, and provide electrical connecting features for detachably connecting a lead passing through the burr hole plug to external stimulating equipment.

In accordance with one aspect of the invention, there is provided a compressible burr hole plug assembly that can be inserted into a variety of burr hole sizes and provides a radial force for positioning the lead. Advantageously, such embodiment is flush with the patient's skull and avoids unsightly flange protrusions which may cause skin erosion.

In accordance with another aspect of the invention, there is provided a burr hole plug assembly that accommodates various lead positions. In addition, the plug assembly provides a secure and flexible adjustment for the lead.

It is an additional feature of the invention to provide a burr hole plug assembly that accommodates excess lead length.

It is another feature of the invention to provide a burr hole plug assembly that includes a connecting feature for allowing a lead passing through the assembly to be detachably connected to other devices, such as an implantable pulse generator. Such feature facilitates the use of a positioning stylet, a temporary cable for testing purposes in the operating room, and other equipment used during the surgical implantation procedure. With such feature, electrical connection between an external stimulation device and the lead can be made at the burr hole plug connector, thereby forming a stimulation system. In such a system, the connecting device includes an extension with a connector that mates with the lead at the burr hole plug assembly. The advantages for electronically connecting the lead at the burr hole include: (1) the risk of lead fracture under the scalp is greatly minimized, if not eliminated; (2) the risk of lead failure at the burr hole exit point is similarly minimized, if not eliminated; (3) the risk of the lead moving in the brain as a result of external disruption is virtually eliminated; and (4) if any part of the system fails external to the skull, brain surgery is not required to replace the system.

BRIEF DESCRIPTION OF THE DRAWINGS

The above and other aspects, features and advantages of the present invention will be more apparent from the following more particular description thereof, presented in conjunction with the following drawings wherein.

Corresponding reference characters indicate corresponding components throughout the several views of the drawings.

DETAILED DESCRIPTION OF THE INVENTION

The following description is of the best mode presently contemplated for carrying out the invention. This description is not to be taken in a limiting sense, but is made merely for the purpose of describing the general principles of the invention. The scope of the invention should be determined with reference to the claims.

Deep Brain Stimulation (DBS) is rapidly becoming an accepted procedure to treat diseases such as Parkinson's Disease, Essential Tremor, dystonia, the relief of chronic pain, and potentially the treatment of choice for other movement disorders. The present invention discloses several burr hole plug assembly embodiments that can be used to seal a burr hole made into a patient's skull in order to allow lead access for stimulating the brain. The significant advantages of the several burr hole plug assembly embodiments presented herein will be described with reference to associated features shown in FIGS. 1A through 11C.

Figure 1A:
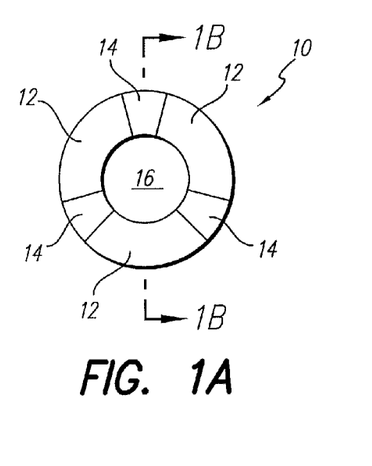
FIG. 1A is a top view showing a compressible burr hole plug ring made in accordance with one embodiment of the invention.
Figure 1B:
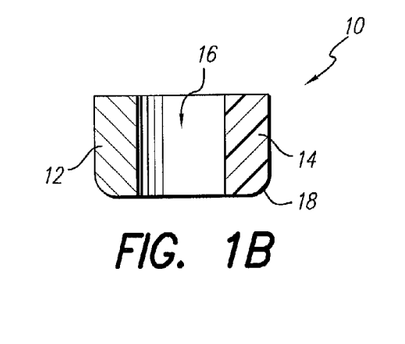
FIG. 1B is a cross sectional view taken along line 1B—1B of FIG. 1A, showing the compressible burr hole plug ring.

Referring first to FIGS. 1A and 1B, there is shown a compressible burr hole plug ring 10. The burr hole plug ring 10 is preferably made from two biocompatible materials, a first rigid material 12 and a second compressible material 14. To maintain adequate rigidity the burr hole plug ring 10 comprises a combination of metal (or hard) member segments 12 and elastic (or compressible) member segments 14. The material for the rigid members 12 is made from epoxy, polyurethane, and titanium, or alloy compounds of epoxy, polyurethane, and titanium, or equivalent materials. The compressible elastic member 14 may comprise a suitable elastomer selected from the group consisting of: silicone rubber, polyurethane, or equivalent materials. A central hole 16 is used for accepting a lead. The bottom edge 18 of the burr plug ring 10 is preferably rounded or chamfered to facilitate entry of the plug ring 10 into the burr hole 20, as shown in FIG. 2A.

Figure 2A:
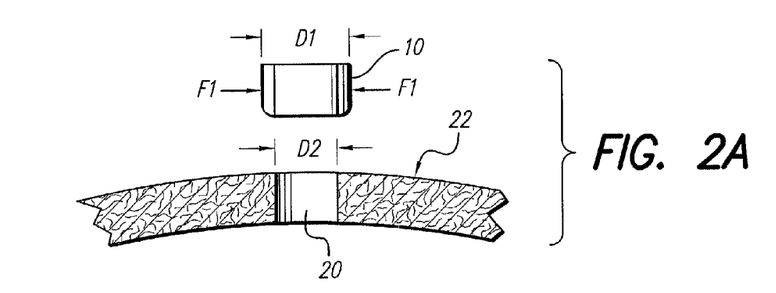
FIG. 2A is a side cross sectional view of the compressible burr hole plug ring before it is placed in the burr hole of the cranium.
Figure 2B:
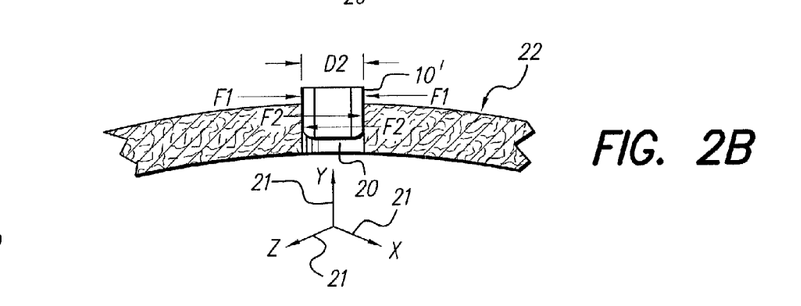
FIG. 2B is a side cross sectional view of a compressible burr hole plug ring as it is placed in the burr hole of the cranium.

As seen in FIG. 2A, the burr hole plug ring 10 has an outside diameter D1 larger than the diameter D2 of the burr hole. The burr ring plug 10 is compressed by an insertion force F1 until its outside diameter D1 equals D2. FIG. 2B shows the compressed burr plug ring 10' inserted into the burr hole 20. The compressible force F1 causes an equal and opposing force F2 to be asserted against the edges of the burr hole of the cranium 22. This force F2 secures the burr hole plug 10' in the patient's skull. Advantageously, the reaction force F2 eliminates the need for ridges on the outer diameter of the plug ring 10, and further eliminates the need for a flange above the skull that acts to limit the motion in the X, Y, and Z directions 21, stabilizing the burr hole plug assembly in the burr hole.

Figure 12:
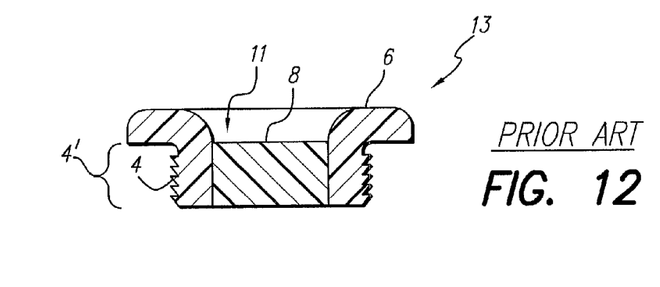
FIG. 12 depicts a prior art embodiment of a burr hole ring with a flange and ridges.

A prior art embodiment of a burr hole assembly 13 with ridges 4, a flange 6 and septum material 8 in central hole 11 is shown in FIG. 12. As is evident from FIG. 12, the flange 6 would protrude above the patients' skull when the ridge section 4' is inserted in the burr hole. Disadvantageously, a protruding flange 6 may cause skin erosion, and creates an unsightly bump in the head, especially in the patient population of older balding males.

Figure 3A:
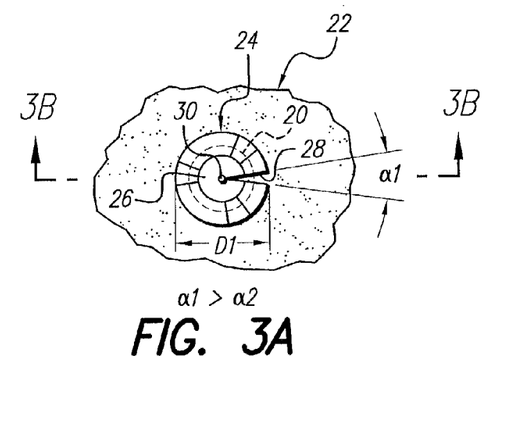
FIG. 3A is a top view of the compressible burr hole plug ring shown in FIG. 1A, and further including septum material positioned in the center of the ring to thereby form a burr hole plug assembly, wherein the septum material has a slit therein used for lead placement before the plug assembly is placed in the burr hole of the cranium.

Referring next to FIG. 3A, there is shown an alternate embodiment of a compressible burr hole plug assembly 24 having a septum material 26 contained within the central hole of the assembly 24 and a slit 28 for placing a lead 30 and/or cannula. Placement of the plug assembly 24 can be done before, during, or after placement of the lead. The septum material 26 may comprise silicone rubber or polyurethane or equivalent materials, and may have a porous or solid composition. When the burr hole plug assembly 24 is compressed in the burr hole, the septum material 26 is also compressed and thus applies a radial force around the lead, thus acting to stabilize the lead 30. The burr hole plug assembly 24 with slit 28 thus enables placement around a lead 30 and/or cannula. The slit also allows for placement of the plug before, during, or after the lead is placed. The lead 30 is properly positioned by a surgeon using an apparatus such as a stereotactic frame. The stereotactic frame is used to precisely localize an area in the brain by means of coordinates related to intra cerebral structures. U.S. Pat. No. 4,350,159, discloses a stereotactic instrument used for precise insertion of an electrode in the brain. The '159 patent is incorporated herein by reference. Once a lead or electrode has been inserted by the surgeon in the localized position of the brain, it is important that the lead remain in place. A slight movement may cause injury to the brain and/or may cause the diagnosed area that is to be stimulated to be missed. Therefore, use of a precise positioning instrument, such as a stereotactic frame disclosed in the '159 patent, or an equivalent device, is preferred.

Figure 3B:
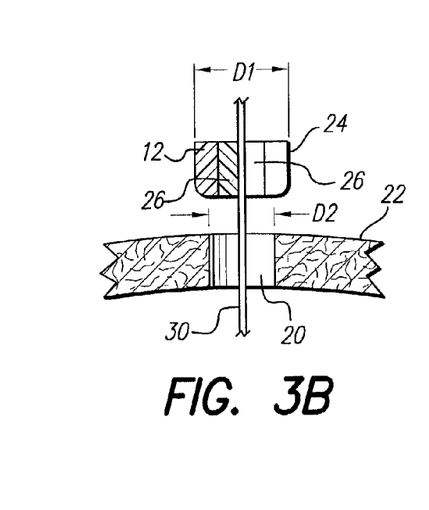
FIG. 3B is a cross sectional view taken along line 3B—3B of FIG. 3A, showing the compressible burr hole plug assembly before it is placed in a burr hole of the cranium.
Figure 3C:
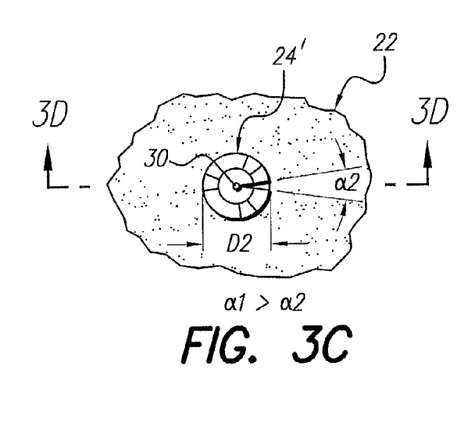
FIG. 3C is a top view of the burr hole plug assembly shown in FIG. 3A after it has been placed in a burr hole of the cranium.
Figure 3D:
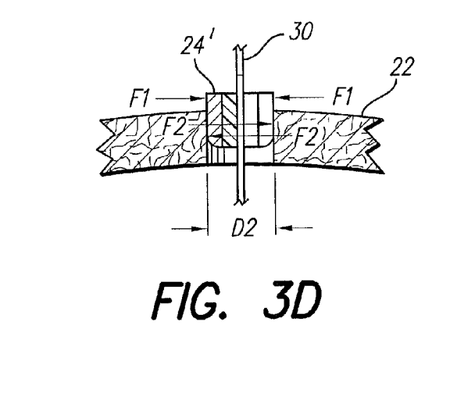
FIG. 3D is a cross sectional view taken along line 3D—3D of FIG. 3C, showing the burr hole plug assembly inserted in the burr hole.

Referring back to FIG. 3A, a top view of the burr hole plug assembly 24 is shown before insertion into the burr hole of the cranium 22 with a slit angle $\alpha 1$. FIG. 3B shows a cross sectional view taken along line 3B—3B of FIG. 3A. As seen in FIG. 3B, the outside diameter D1 of the burr hole plug assembly 24 is larger than the diameter D2 of the burr hole 20. The burr hole plug assembly 24 is compressed by the force F1 until its outside diameter D1 equals D2. FIG. 3C shows the compressed burr hole plug assembly 24' inside the burr hole 20. At the compressed stage of the burr hole plug assembly 24, it can be seen that the angle $\alpha 2$ is less than the angle $\alpha 1$. The compressible force F1 causes an opposing radial force F2 to be generated, which opposing force secures the burr hole plug assembly in the patients' cranium 22 as shown in FIG. 3D. FIG. 3D is a cross sectional view taken along line 3D—3D of FIG. 3C. The compressed burr hole plug assembly 24' and septum material 26 also maintains the lead 30 in the localized position established by the physician.

Figure 4A:
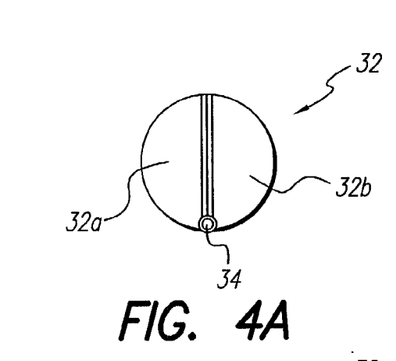
FIG. 4A is a top view of another embodiment of a burr hole plug assembly made in accordance with the invention, which embodiment has a pivot point clamped configuration.
Figure 4B:
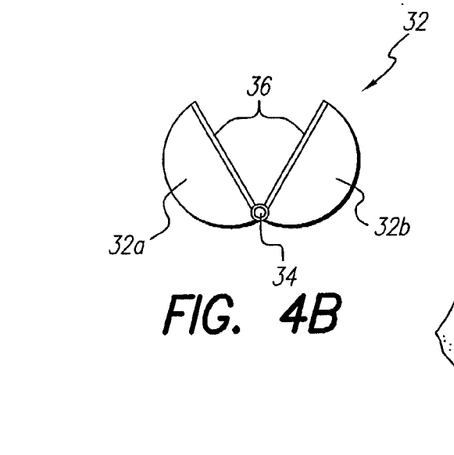
FIG. 4B is a top view of the assembly of FIG. 4A showing the clamp plug assembly in an open arrangement.

Turning next to FIGS. 4A and 4B, there is shown a top view of an alternate embodiment of a clamp plug assembly 32 having a pivot point 34 and two half portions 32a and 32b. The embodiment shown in FIGS. 4A and 4B has a clamp plug assembly 32 that accommodates multiple lead exit trajectories 38. The clamp arrangement of the burr hole plug assembly has the advantage that it can be placed around a lead and/or a cannula regardless of the exit point of the lead from the burr hole trajectory 38 shown in FIG. 5A. FIG. 4B shows the open position of the clamp plug assembly 32. Each half portion 32a and 32b of the clamp plug assembly 32 preferably has an edge material or coating 36, such as silicone, that provides an elastic component that minimizes crushing of the lead when anchored in the clamp plug assembly 32.

Figure 5A:
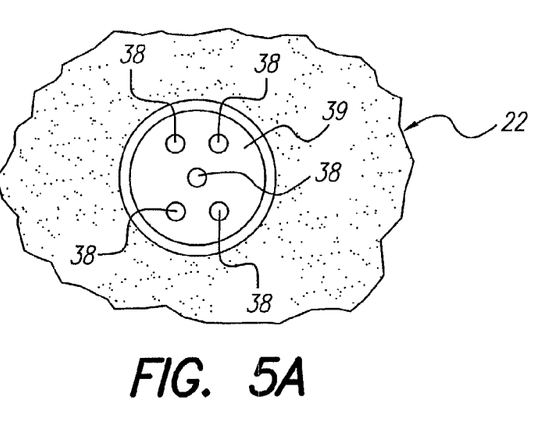
FIG. 5A is a top view of a burr hole and burr hole ring arrangement having multiple lead exit trajectories.
Figure 5B:
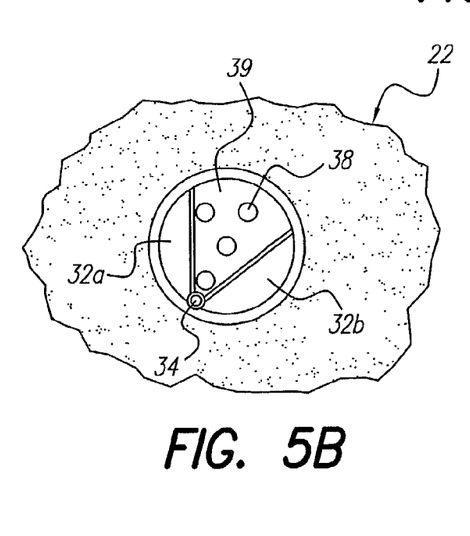
FIG. 5B is a top view of a clamp plug assembly accommodating one arrangement of lead exit trajectories.
Figure 5C:
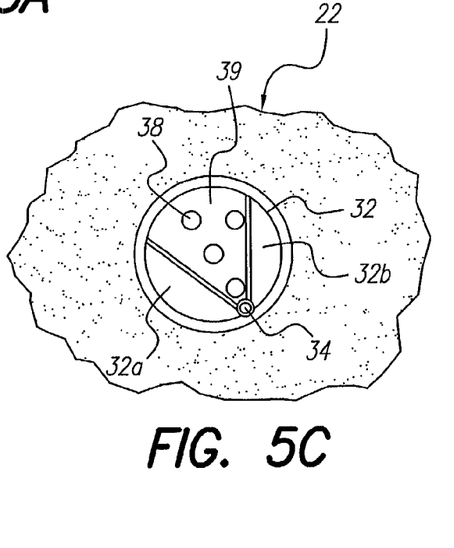
FIG. 5C is a top view of a clamp plug assembly accommodating another arrangement of lead exit trajectories.

FIG. 5A is a top view of a burr hole 39 showing five possible lead exit trajectories 38. The number of trajectories can vary depending on the size of the burr hole 39 and target stimulation site. FIGS. 5B and 5C show the pivot point of the clamp plug assembly 32 in the burr hole 39 in two arrangements accommodating various lead exit trajectories 38.

Figure 6A:
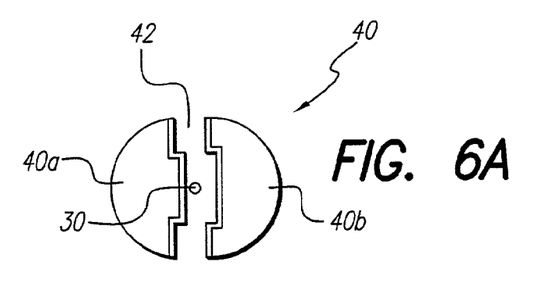
FIG. 6A is a top view of the burr hole plug assembly shown in an open configuration.
Figure 6B:
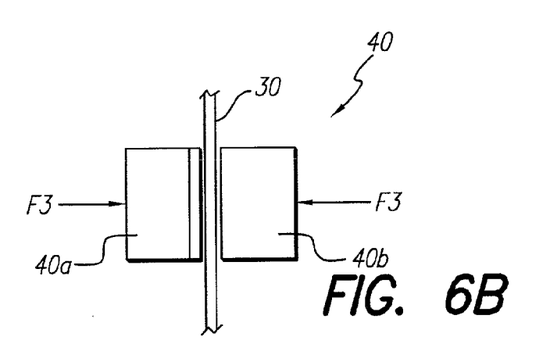
FIG. 6B is the side view of FIG. 6A, showing the open configuration of the burr hole plug assembly with a lead passing therethrough.
Figure 6C:
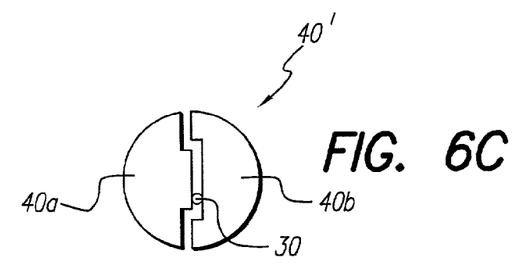
FIG. 6C is a top view of another embodiment of a burr hole plug assembly providing a clamped configuration.
Figure 6D:
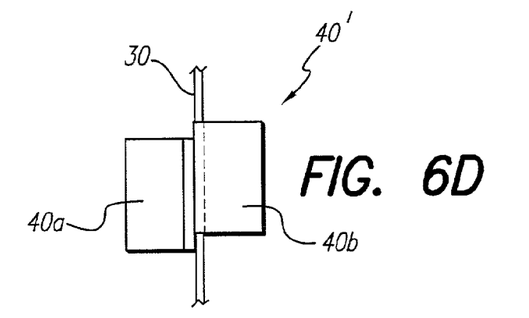
FIG. 6D is the side view of FIG. 6C, showing the clamped configuration of the burr hole plug assembly with a lead passing therethrough.

Next with reference to FIG. 6A and FIG. 6B, there is shown a top and side view respectfully of an alternate embodiment of a splitable burr hole plug assembly 40. The central slit 42 created by the two sliding half portions 40a and 40b of the splitable burr hole plug assembly allows flexibility for positioning the lead. The same half portions 40a and 40b may also have a clamping burr hole plug arrangement 40' as shown in FIG. 6C and FIG. 6D. Once the lead is positioned, the two half portions 40a and 40b are closed. The lead 30 remains in its clamped position due to the force F3 applied by the two half portions 40a and 40b. It is obvious to one skilled in the art that different splitable burr hole configurations are possible.

Figure 7A:
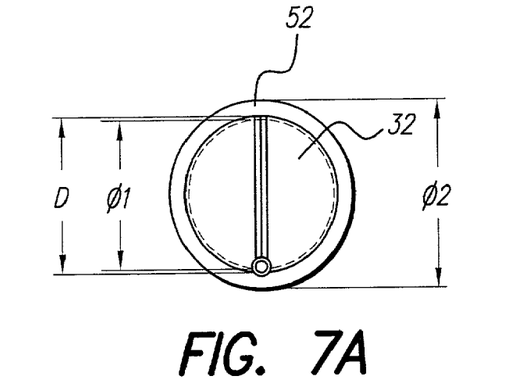
FIGS. 7A, 7B, and 7C are similarly all top views of various burr hole plug rings having different outside diameters to accommodate burr hole plugs of different diameters, and further showing a clamp plug assembly as an example of a type of plug that may be inserted in the rings.
Figure 7B:
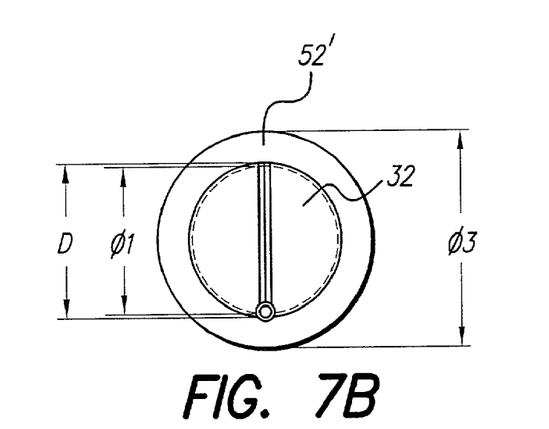
Figure 7C:
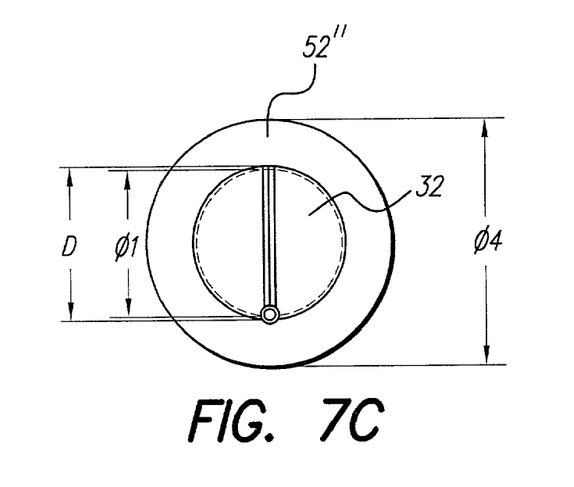

Referring now to FIGS. 7A, 7B and 7C, there is shown a series of O-ring shaped inserts 52, 52', and 52" that can accommodate various size burr holes. Depending on the drill tool that a surgeon may prefer to use during the drilling process of a burr hole in the patients' skull, each burr hole may differ in size from patient to patient and surgeon to surgeon. Therefore, the need for having a variety of inserts is advantageous to the surgeon. The inserts shown in FIGS. 7A, 7B, and 7C each have different outside diameters Ø2, Ø3, and Ø4, respectively, and similar inside diameters Ø1 which can accommodate the same burr hole plug. The inside diameter Ø1 of the inserts may be slightly smaller than the outside diameter D of the preferred plug. For example, FIGS. 7A, 7B, and 7C show the same pivot point clamp plug assembly 32, having two halves 32a and 32b, and a diameter D, as shown in FIG. 4A, inserted in the central hole of the O-ring type inserts 52, 52', and 52". The inserts 52, 52', and 52" exert a force on the clamp plug assembly 32 to keep the two halves in a closed position.

Figure 8A:
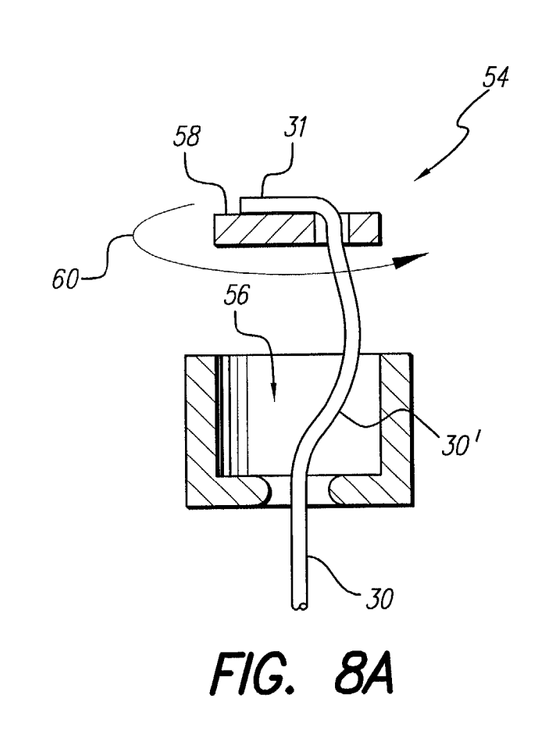
FIGS. 8A, 8B, and 8C are side cross sectional views showing an offset burr hole plug assembly cap which coils excess lead length in a cavity of the assembly as the burr hole cap is rotated.
Figure 8B:
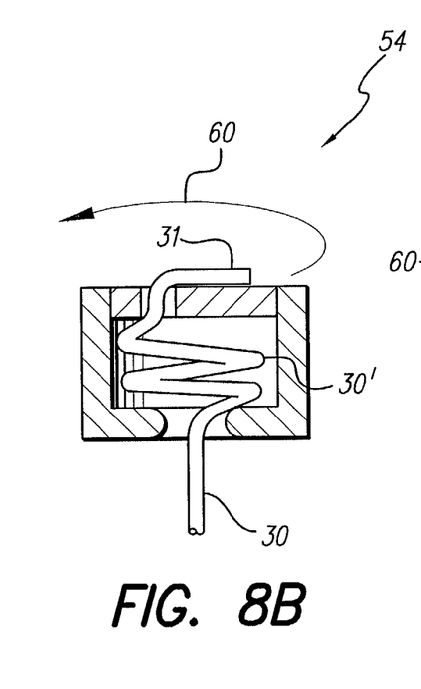
Figure 8C:
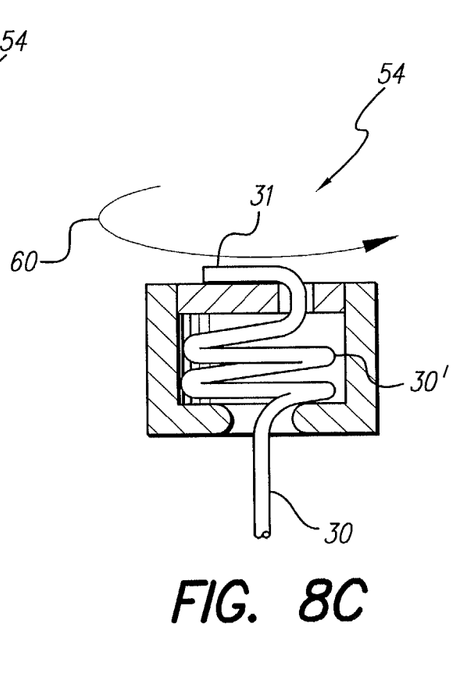

Turning next to FIG. 8A, there is shown a cross sectional view of an alternate embodiment of a burr hole plug assembly 54 having a hole cavity 56 and a plug cap 58. The plug cap 58 enables wrapping excess lead length 30' in the hole cavity 56 of the burr hole plug assembly 54. The external end 31 of the lead 30 is attached to the cap 58. The cap 58 is then rotated as shown by the arrow 60 in FIG. 8A, which rotating causes the lead length to be coiled within the hole cavity 56, as seen in the sequence of FIGS. 8A, 8B and 8C. The height of the excess lead length and corresponding turns required to wrap the lead in the cavity 56 of the burr hole plug 54 varies, depending on the type of stereotactic frame used to position the lead. Other factors that may vary, depending on the frame used are, the working lead length, the target distance (which is the distance measured from the surface of the skull to a reference point in the frame), the size of the burr hole, the lead diameter, and patient differences. As an example, for a burr hole size of 8 mm and a lead diameter of 1 mm, the Leksell Stereotactic System manufactured by Elekta AB, located in Stockholm Sweden, would require a working lead length of 190 mm, a target site length of 85 mm, an excess lead length of 105 mm, and 4.2 turns to wrap the excess lead length 30' in the offset hole cavity 56. Another type of stereotactic frame available is the CRW Arc System manufactured by Radionics, located in Burlington Mass. As an example, for a burr hole size of 8 mm and a lead diameter of 1 mm, the CRW Arc System requires a working lead length of 160 mm, a target site length of 85 mm, an excess lead length of 75 mm, and 3.0 turns to wrap the excess lead length 30' in the offset hole cavity 56. Other examples of excess lead length and corresponding number of turns in a burr hole plug cavity exist for various burr hole sizes and targets used in conjunction with the CRW and Leksell systems.

Figure 9A:
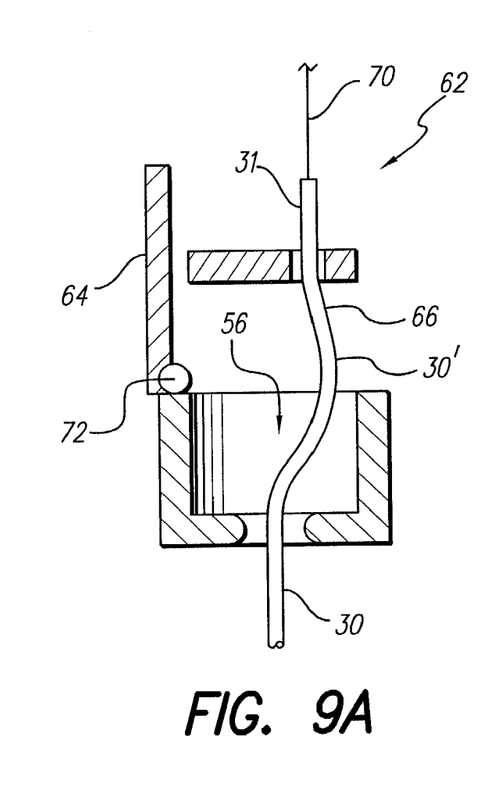
FIGS. 9A, 9B, and 9C are side cross sectional views showing various positions of the same offset burr hole plug cap shown in FIGS. 8A, 8B, and 8C, and additionally illustrating the use of a "snap-cap" connector therewith.
Figure 9B:
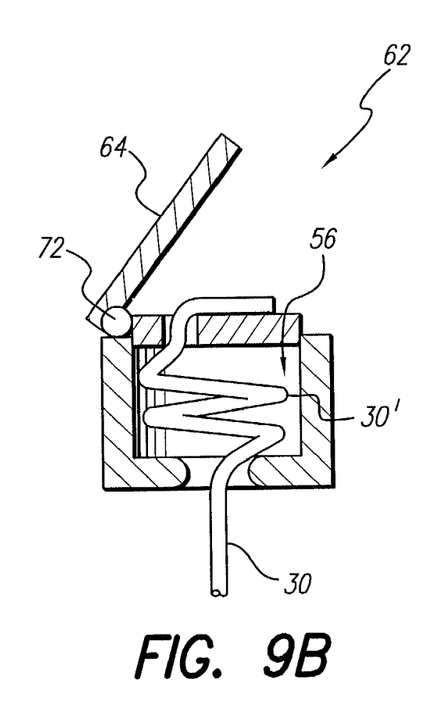
Figure 9C:
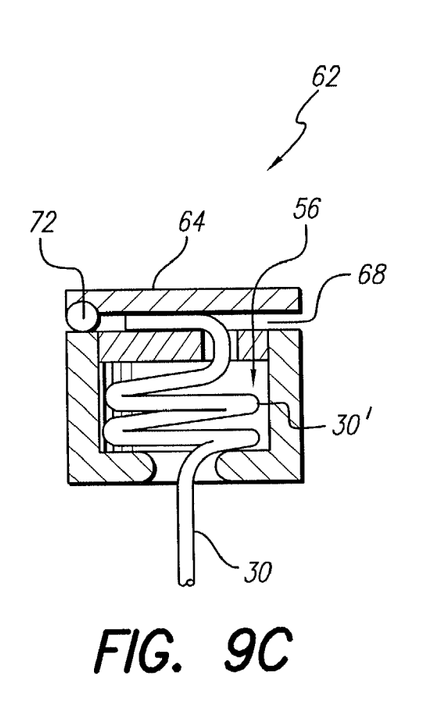

An alternate embodiment of an offset burr hole plug assembly 62 is shown in FIG. 9A. The same principle for positioning the lead 30 and rotating the excess lead length 30' in the cavity 56 of the offset burr hole plug 62 is similar as explained for FIGS. 8A, 8B, and 8C. Corresponding adjusting factors for the lead 30 with respect to the type of stereotactic frame used are also similar as explained above. The additional feature found in the embodiment shown in FIG. 9A is an integral "snap-cap" connector 64. The connector 64 can accommodate a temporary cable for testing purposes in the operating room or become a permanent connector to the implantable pulse generator, not shown. The proximal end 31 of the lead shown in FIG. 9A can be preformed in a bent configuration 66 to reduce the stress on the lead 30 at the connector location 68. Also shown in FIG. 9A, when the lead has a lumen therein, a stylet 70 may be inserted into the lumen, and the preformed section of the lead would be straightened. Such stylet, if used, would be used only during the initial insertion and placement of the lead through the burr hole. The stylet 70 is removed before the excess lead length is coiled within the cavity 56. FIGS. 9B and 9C are cross sectional views of the offset burr hole plug assembly 62, showing the rotated excess lead length 30' in the plug assembly's cavity 56, and also showing the connector closed by the pivot point 72.

Figure 10A:
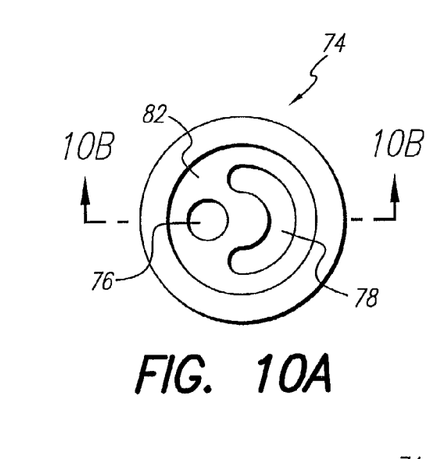
FIG. 10A is a top view of yet another embodiment of an offset burr hole plug assembly having a stabilizing access hole for capturing and securing the lead.
Figure 10B:
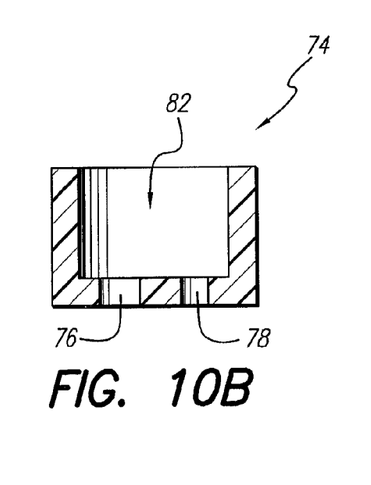
FIG. 10B is a cross sectional view taken along line 10B—10B of FIG. 10A; showing the offset burr hole plug assembly with a stabilizing access hole.
Figure 10C:
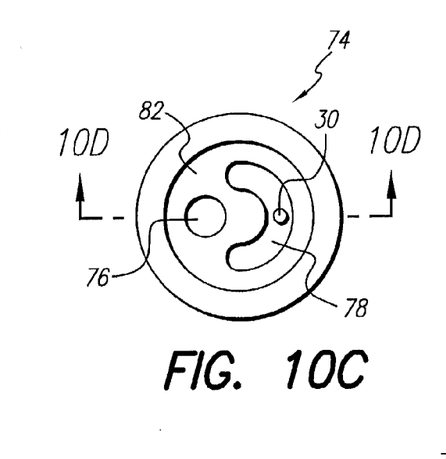
FIG. 10C is a top view of the same offset burr hole plug assembly shown in FIG. 10A but with a lead placed in the stabilizing access hole.
Figure 10D:
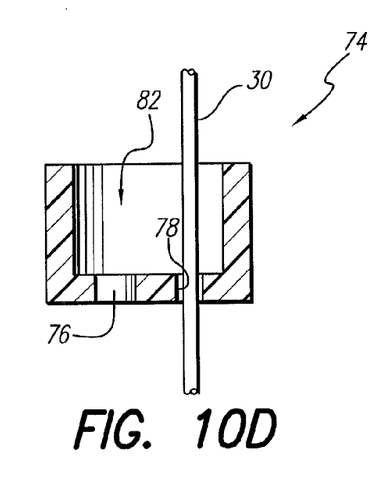
FIG. 10D is a cross sectional view taken along line 10D—10D of FIG. 10C; showing the offset burr hole plug and lead.
Figure 10E:
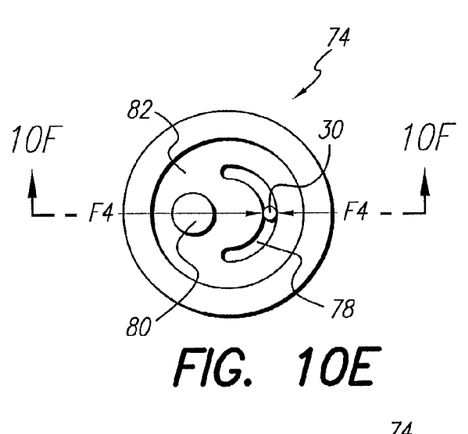
FIG. 10E is a top view of the same burr hole plug shown in FIG. 10A with the lead stabilized through a force exerted by insertion of a placement pin.
Figure 10F:
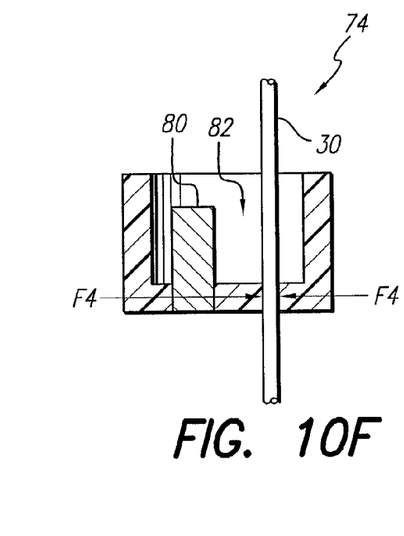
FIG. 10F is a cross sectional view taken along line 10F—10F of FIG. 10E; showing the offset burr hole plug assembly and stabilized lead.

Another alternate embodiment of an offset burr hole plug assembly 74 is shown in FIGS. 10A and 10B. FIG. 10A is a top view of the offset burr hole plug assembly 74 and FIG. 10B is a cross sectional view taken along line 10B—10B of FIG. 10A. The offset burr hole plug assembly 74 is made of an elastic biocompatible material and contains two openings, a pin hole 76 and a semi-circular slot hole 78. The semi-circular slot hole 78 captures the lead 30 and the pin hole 76 accommodates a fixation rod 80. FIG. 10C shows the lead 30 in the semi-circular slot hole 78 and FIG. 10D is a cross sectional view taken along line 10D—10D of FIG. 10C. When the fixation rod 80 is inserted into pin hole 76, a force F4, shown in FIGS. 10E and 10F, is exerted against the lead 30, which in effect stabilizes the lead 30, and holds the lead in its desired position. The fixation rod 80 may also act as an axis for rotating the excess lead length around the cavity 82 of the offset burr hole plug 74, if needed or desired. FIG. 10F is a cross sectional view of FIG. 10E taken along the line 10F—10F of FIG. 10E.

The offset burr hole plug assembly 74 shown in FIGS. 10A through 10F can also accommodate a "snap-cap" connector 64, shown in FIG. 9A, a "plug-in" connector 86, shown in FIG. 11B (discussed below), and variable size inserts 52, 52', and 52" shown in FIGS. 7A, 7B, and 7C. In the case of using the "plug-in" connector 86, an offset burr hole plug ring 84 has a radius groove 88, shown in FIG. 11A, to minimize the stress of the bend of the lead exiting the offset burr hole plug ring 84.

Figures 11A, 11B, 11C:
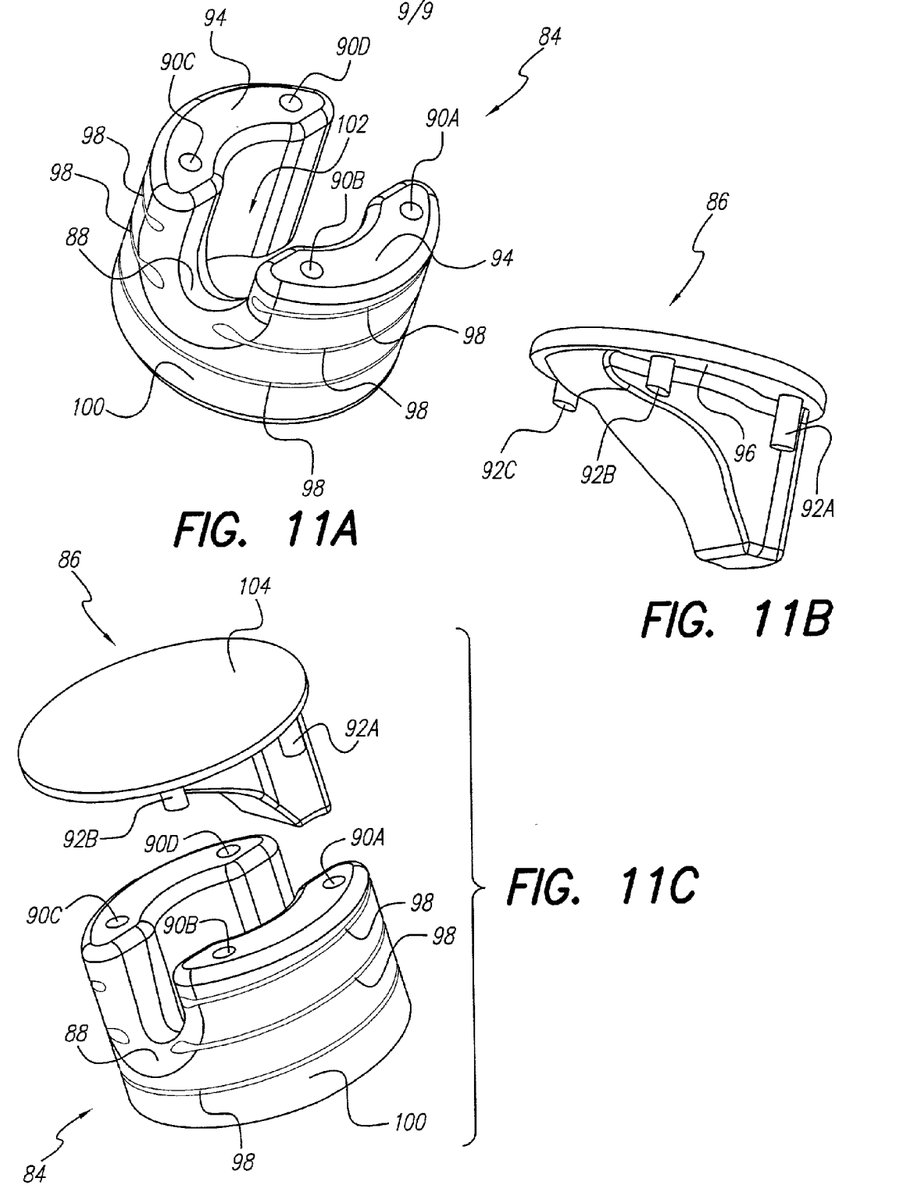
FIG. 11A shows another embodiment of a burr hole plug assembly ring made in accordance with the invention.
FIG. 11B illustrates a "plug-in" connector used in conjunction with the burr hole plug assembly ring shown in FIG. 11A.
FIG. 11C is an exploded view of the burr hole plug assembly, showing the ring of FIG. 11A and "plug-in" connector of FIG. 11B.

Next, with reference to FIGS. 11A, 11B, and 11C, another embodiment of a burr hole plug ring 84 with an integral "snap-cap" connector 86 is shown. The burr hole plug ring 84 can accommodate a temporary connector at surface 104 for testing in the operating room and a permanent connector to the implantable pulse generator, not shown in the figures. In one embodiment, the temporary connector could also serve as the tool for inserting the burr hole plug ring 84 into the burr hole of the cranium. The burr hole plug ring 84 is shown with a radius groove 88. The radius groove 88 minimizes the stress of the bend of the lead 30 exiting the burr hole plug ring 84. Insertion holes 90A, 90B, 90C, and 90D are located on the exposed surface 94 of the burr hole plug ring 84 which accommodate corresponding connecting pins 92A, 92B, 92C, and 92D (not shown) located in the bottom surface 96 of the "snap-cap" connector 86. As shown in FIG. 11A, ridges or threads 98 exist in the outer surface 100 of the burr hole plug ring 84. The ridges or threads 98 screw into the burr hole to stabilize the burr hole plug ring 84 into the burr hole. The opening 102 through the ring 84, goes through the entire thickness of the burr hole plug ring 84 and provides the entrance for the lead into the diagnosed stimulating area of the brain. In addition, the burr hole plug ring 84 can also accommodate the inserts 52, 52', and 52", shown in FIGS. 7A, 7B, and 7C, thereby allowing the plug ring 84 to be used with various sizes of burr holes.

As described above, it is thus seen that the present invention provides several burr hole plug embodiments (10, 24, 32, 40, 54, 62, 74, and 84), shown in FIGS. 1A through 11C. Each embodiment provides various advantages in providing a passage for a lead, ablation catheters, drug delivery catheters, tissue delivery catheters, etc. Microelectrode recording equipment and macroelectrode stimulation equipment can also be placed through the burr hole plug. Some embodiments contain a septum material or soft polymer that allows passage of all equipment and that also exert a radial force which in turn stabilizes the inserted lead or equipment. Other embodiments are made from a combination of rigid and compressible material which when compressed provide a reaction force which also stabilizes the inserted lead or equipment.

While the invention herein disclosed has been described by means of specific embodiments and applications thereof, numerous modifications and variations could be made thereto by those skilled in the art without departing from the scope of the invention set forth in the claims.

What is claimed is:

1. A cranial sealing plug assembly adapted for insertion into a burr hole having a size D2 made in a patient's skull, comprising:

a burr hole plug ring insertable into the burr hole so as to be flush with the patients skull, the plug ring having an opening through its center which allows access into the burr hole; and a sealing member that seals the opening through the center of the plug ring;

wherein the burr hole plug ring has a diameter D1 that is slightly larger than the size D2 of the burr hole, thereby creating a compression force that prevents movement of a lead passing through the sealing member; and wherein the compression force further stabilizes the burr hole plug assembly in the burr hole.

2. The cranial sealing plug assembly of claim 1 wherein the sealing member comprises a septum.

3. The cranial sealing plug assembly of claim 1 wherein the burr hole plug ring includes at least one segment made from a compressible biocompatible material, and at least another segment made from a noncompressible biccompatible material.

4. The cranial sealing plug assembly of claim 3 wherein the there are at least two segments made from the compressible biocompatible material, and at least three segments made from the non-compressible biocompatible material.

5. The cranial sealing plug assembly of claim 3 wherein the compressible biocompatible material compresses an elastomer selected from the group consisting of: silicone rubber and polyurethane.

6. The cranial sealing plug assembly of claim 3 wherein the non-compressible biocompatible material is selected from the group consisting of; epoxy, polyurethane, and titanium, and alloy/compounds of epoxy, polyurethane, and titanium.

7. The cranial sealing plug assembly of claim 1 wherein the sealing member and burr hole plug ring have a radial slit therein for accommodating a lead or cannula passing therethrough.

8. The cranial sealing plug assembly of claim 1 further including at least one O-ring insert adapter having an outer diameter adapted to snugly fit within the burr hole, and an inner diameter adapted to receive the plug assembly.

9. The cranial sealing plug assembly of claim 8 further including a plurality of O-ring insert adapters, each having a different outer diameter adapted to snugly fit within respective burr holes of varying sizes, and each having an inner diameter adapted to receive the plug assembly, whereby the plug assembly may be inserted into burr holes of varying sizes.

* * * * *